United States Patent
Frazee et al.

(10) Patent No.: US 10,106,511 B2
(45) Date of Patent: Oct. 23, 2018

(54) CONTINUOUS HIGH SHEAR REACTOR MELT PROCESSING METHODS TO SYNTHESIZE HETEROCYCLIC MONOMERS AND COMPOSITIONS THEREOF

(71) Applicants: Andrew S. Frazee, Hattiesburg, MS (US); Jeffrey S. Wiggins, Petal, MS (US)

(72) Inventors: Andrew S. Frazee, Hattiesburg, MS (US); Jeffrey S. Wiggins, Petal, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 0 days.

(21) Appl. No.: 15/367,075

(22) Filed: Dec. 1, 2016

(65) Prior Publication Data

US 2017/0166537 A1 Jun. 15, 2017

Related U.S. Application Data

(60) Provisional application No. 62/261,798, filed on Dec. 1, 2015.

(51) Int. Cl.
*C07D 265/16* (2006.01)
*C07D 207/404* (2006.01)
*C08G 73/10* (2006.01)

(52) U.S. Cl.
CPC ....... *C07D 265/16* (2013.01); *C07D 207/404* (2013.01); *C08G 73/1092* (2013.01)

(58) Field of Classification Search
CPC ...................................................... C08G 73/92
USPC ........................................................... 544/90
See application file for complete search history.

(56) References Cited

U.S. PATENT DOCUMENTS 5,543,516 A * 8/1996 Ishida .................. C07D 265/16
544/69

* cited by examiner

*Primary Examiner* — Kahsay Habte
(74) *Attorney, Agent, or Firm* — Lawrence Arthur Schemmel (57) ABSTRACT

The invention provides novel methods of synthesizing new monofunctional and/or multifunctional heterocyclic monomers and the formulation of new alloys of said monomers from base reactants via a continuous solvent-free, or alternatively in-solvent, one-step high shear reactor methodology designed to reduce the minor isomer formation and to eliminate the need for post-processing purification, as well as the ability to disperse reinforcements and additives while synthesizing such heterocyclic monomers and monomer alloys created and to the synthesis of related compositions.

16 Claims, 5 Drawing Sheets

CONTINUOUS HIGH SHEAR REACTOR MELT PROCESSING METHODS TO SYNTHESIZE HETEROCYCLIC MONOMERS AND COMPOSITIONS THEREOF

CROSS-REFERENCE TO RELATED APPLICATION

This application claims priority from U.S. Provisional Patent Application Ser. No. 62/261,798 filed Dec. 1, 2015. The entirety of the provisional application is incorporated herein by reference.

FIELD OF THE INVENTION

This invention relates to the field of thermoset composite matrix production and processing and, more specifically, to novel methods of synthesizing monofunctional and/or multifunctional heterocyclic monomers and the formulation of alloys of said monomers via a continuous, solvent-free, or alternatively in-solvent, one-step methodology designed to reduce isomer formation and to eliminate the need for post-processing purification, and to the synthesis of related compositions.

SUMMARY OF THE INVENTION

The present invention provides a novel solvent-free, or alternatively in-solvent, continuous high shear reactor adept to synthesize monofunctional and/or multifunctional heterocyclic monomers and to formulate heterocyclic monomer alloys comprised of said monomers from base reactants in a single-step continuous method. Specifically, the invention allows the synthesis of the aforementioned monomers without the need for purification and reduced isomer content. Furthermore, the invention discloses the ability to synthesize alloys comprised of these monomeric species.

The invention also provides the ability to disperse reinforcements and additives while synthesizing heterocyclic monomers and monomer alloys created by the methods and system of the invention.

With the foregoing and other objects, features, and advantages of the present invention that will become apparent, the nature of the invention may be more clearly understood by the following detailed description of the preferred embodiments of the invention and by the appended claims.

BACKGROUND OF THE INVENTION

Heterocyclic chemistries such as benzoxazines have previously been synthesized in solvent-free and single-screw reactors. However, a single-step, solvent-free synthesis methodology of heterocyclic monomers (monofunctional and/or multifunctional) with increased reaction efficiency and elimination of post-processing purification is unreported in the current scientific and patent literature. The present invention disclosed herein provides such novel methodologies whereby a continuous, high shear reactor is comprised of at least one co-rotating twin-screw extruder, which is highly modular with respect to structural design, feed delivery systems, and experimental parameters, for example, but not limited to processing temperature, residence time, screw speed, and/or screw design.

The solvent-free, continuous high shear reactor methods and system of the present invention provide a cost-effective, environmentally-favorable, and scaleable method to synthesize heterocyclic monomers and the alloys thereof. The invention alternatively can be utilized in-solvent. The heterocyclic monomers of the invention were synthesized in about 30-60 seconds and without the need for post-processing purification, as opposed to current technology claiming reaction times of 30-60 minutes with the need for purification.

Benzoxazine: Synthesis, Properties, and Composites

Developments in Heterocyclic Chemistries:

Benzoxazines are heterocyclic compounds synthesized by reacting a phenolic derivative, primary amine, and paraformaldehyde as first reported by Holly and Cope in 1944. From this breakthrough came fundamental and exploratory studies investigating benzoxazine chemistries and applications, but it was not until the 1980s when Higginbottom discovered multifunctional benzoxazines and potential opportunities as thermosetting matrices. Although advancements in benzoxazine matrix chemistries continued to proliferate, the novelty and unique properties of benzoxazines were not realized until the 1990s by Ishida et al. following a thermally-activated, ring-opening polymerization study. Although the ring-opening mechanism is not clearly understood, a proposed mechanism is provided in Scheme 1.

Scheme 1: Benzoxazine cationic ring opening polymerization mechanism.

-continued

The unique properties of multifunctional benzoxazine chemistries for thermoset matrices include modular molecular design, long shelf-life, cost-effectiveness, high Tg, high modulus, good fire resistance properties, low moisture absorption, no by-products during cure, near-zero chemical shrinkage, and self-curing upon thermal activation. Despite the remarkable properties of multifunctional benzoxazines, their unfavorable processability is one of the primary shortcomings of benzoxazine chemistries in commercial markets.

Multifunctional benzoxazine monomers are typically glassy solid powders at temperatures below 120° C., making them difficult to process in aerospace applications such as filming and prepregging. Research focused on improving the processability of multifunctional monomers discovered their ability to form an alloy with other matrix chemistries affording tailorable physical properties and solvent-free processing. Currently, multifunctional monomers blended with reactive diluents (i.e. epoxies) are commercially available, but the desirable properties of benzoxazines are significantly reduced by the high dilution of epoxies needed to achieve liquid physical states favorable for processing. Alternatively, studies by Ishida et al. and Cytec Engineered Materials focused on utilizing liquid monofunctional benzoxazine monomers as reactive diluents. Another shortcoming of benzoxazine chemistries is due to current need to use solvents for their synthesis in batch reactors. The use of energy intensive batch reactors and the cost of proper handling and extraction of solvents from the final product have made benzoxazines cost-prohibitive for many applications.

Bismaleimide (BMI) matrix chemistries and their analogues are another example of a heterocyclic chemistry that is increasing in demand for high-performance applications, such as carbon fiber prepreg. BMI systems are thermally cured through an addition reaction yielding matrices with high Tg, thermal stability, and fire resistance. Similarly to benzoxazines, one of the primary shortcomings of BMI chemistries is due to their lack of processability. More specifically, BMI chemistries are synthesized commercially in batch reactors that require the use of solvent and high temperatures. The use of energy intensive batch reactors, the cost of proper handling and extraction of solvents during manufacturing, and consumer demand for high purity and solvent-less products affords the need for an alternative processing method such as the present invention.

Continuous Chemical Reactors

Continuous Reactive Processing:

With international attention of media and consumers focused on sustainability, "green" manufacturing is an area of technology for which global and regional governmental agencies and corporations are willing to pay a premium to reduce emissions, energy consumption, and toxic substances. Polymerization reactors and processes (i.e. batch systems) are commonly energy intensive and produce inconsistent product quality. The production of epoxies used as structural matrices in fiber reinforced aerospace materials provides a great example. In this process, a batch reactor is charged with large volumes of monomer (epoxy and amine) and tougheners (thermoplastic) to which heat is applied to advance molecular weight, forming "b-staged" epoxy prepolymers. These prepolymers are then discharged and stored in freezers to reduce continued reactions until reheated and applied as a thin film for prepreg manufacturing. The energy consumption from batch heating, sub-ambient storage, and filming results in substantial production costs. Nonetheless, elevations in direct manufacturing costs are incurred from batch-to-batch variations in material quality and opportunity costs from downtime and accumulated inventory during the sub-ambient storage.

Advancements in twin screw extrusion technology for thermoplastic compounding and continuous polymerization reactors have matured since the initial concepts proposed by Wunsche and Easton in the early 1900s. As reported in the literature by Brown & Orlando and Xanthos, process capabilities for twin screw extruders (TSE) have expanded as continuous reactors, bulk polymerization reactors, polymer grafting reactors, and polymer blend compatibilization reactors. Compared to batch reactors, the primary advantage of reaction extrusion is credited to the extruder's ability to transport a broad range of viscosities and molecular weights simultaneously. Furthermore, the absence of solvent coupled with low volume processing and high throughputs improve energy consumption affording an environmentally-favorable reactive process. TSE process designs are extremely modular offering precision feeding, mixing, controlled shear energies, excellent heat transfer, insensitivity to viscosity changes, and devolatilization.

Modular Processing Designs of Continuous Chemical Reactors:

It is well-documented that fully intermeshing co-rotating twin screw extruders provide the highest level of mixing, dispersion, and shear control, making them the primary unit for continuous chemical reactors. Intermeshing co-rotating twin screw extruders offer a multitude of screw elements providing modularity in the screw design to achieve effective material transport, mixing, and shear. Examples of typical intermeshing co-rotating modular screw elements for screw designing are various flighted conveying elements, kneading blocks (neutral, right, and left), and ZME. The most common continuous reactor screw design includes conveying elements, kneading elements, and mixing elements.

Reactor screws are designed specifically for the material and the targeted function of the process (i.e. blending, dispersing, etc.). Reactor screws are precision tolerance fit within a series of "barrel sections" that are independently temperature-controlled. Additionally, the barrel sections are interchangeable providing the flexible design of inlets to various liquid reactants, solid reactants, and catalysts, as well as vacuum ports for devolatilization along the reactor. A common processing section of a continuous chemical reactor comprises modular components including barrel sections, liquid feed, solid feed, and twin screws, for example.

The present invention discloses novel continuous high shear reactor providing a cost-effect, environmentally-favorable, and scaleable design methods to synthesize heterocyclic monomers (monofunctional and/or multifunctional) with increased reaction efficiency and elimination of post-processing purification. Furthermore, the high shear environment enables the simultaneous dispersion of reinforcements and additives while synthesizing the heterocyclic monomers.

BRIEF DESCRIPTION OF THE DRAWINGS

The drawings and Figures shown within the specification accompany the detailed description of the invention and are intended to illustrate further the invention and its advantages. The drawings and Figures, which are incorporated in and form a portion of the specification, illustrate certain preferred embodiments of the invention and, together with the entire specification, are meant to explain preferred embodiments of the present invention to those skilled in the art. Relevant FIGURES are as follows.

DETAILED DESCRIPTION OF THE INVENTION

The invention provides methods of synthesizing novel monofunctional and/or multifunctional heterocyclic monomers and the formulation of novel alloys of said monomers from base reactants via a continuous solvent-free, or alternatively in-solvent, one-step high shear reactor methodology designed to reduce the minor isomer formation and to eliminate the need for post-processing purification. Moreover, the invention provides the ability to disperse reinforcements and additives while synthesizing such heterocyclic monomers and monomer alloys created and provides for the synthesis of related compositions. All parameters presented herein including, but not limited to, temperatures, pressures, times, sizes, amounts, ratios, weights, and/or percentages, for example, represent approximate values. References to 'a' or 'an' concerning any particular item, component, material, or product is defined as at least one and could be more than one.

The present invention provides for new methods to synthesize monofunctional and/or multifunctional benzoxazine and/or maleimide and/or bismaleimide monomers from any known variant of the base reactants in molar ratios of about 1:1:4, phenol:amine:paraformaldehyde, for monofunctional benzoxazines, or in molar ratios of about 1:1:8, phenol:amine:paraformaldehyde, for multifunctional benzoxazines, or in molar ratios of about 1:3 primary amine:maleic anhydride for maleimides, and for multifunctional bismaleimides, for example, without the need for post-processing purification in a single-step and solvent-free, or alternatively an in-solvent, design. Simultaneously, the invention also provides the ability to disperse reinforcements and additives with the synthesized monomers.

Figure 1:
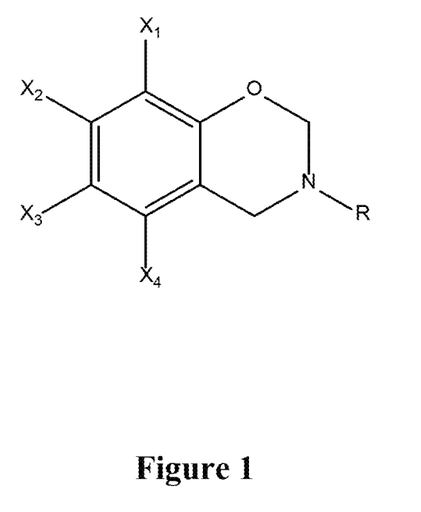
FIG. 1 depicts monofunctional benzoxazine monomer general structures of the present invention.
Figure 2:
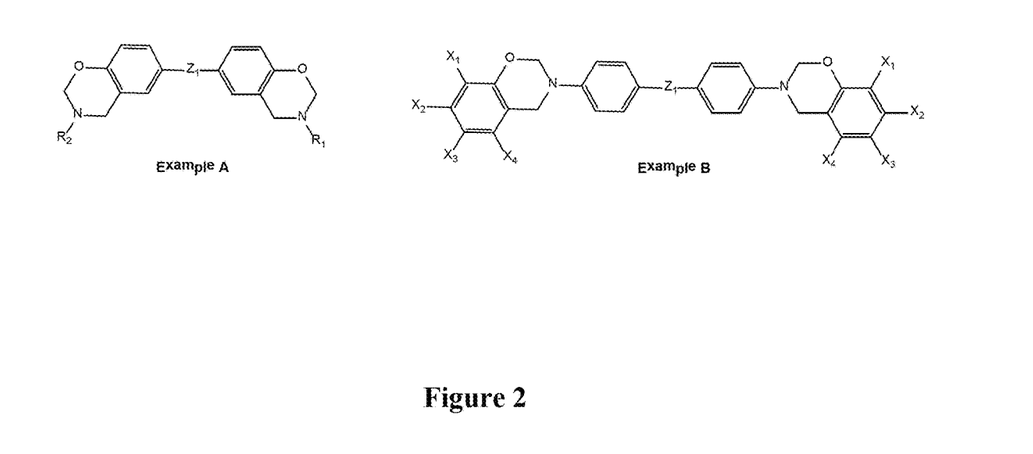
FIG. 2 depicts multifunctional benzoxazine monomer general structures of the present invention.

The invention relates to the melt synthesis of any monofunctional (FIG. 1) and/or multifunctional (FIG. 2) benzoxazine or any monofunctional (FIG. 3) maleimide or multifunctional (FIG. 4) bismaleimide monomer in the application of heterocyclic matrices for high performance thermoset composites. Specifically, the invention pertains to variants of monofunctional benzoxazine monomers, as in FIG. 1, wherein substituents $X_{1-4}$ on phenol can be an electron withdrawing group, for example but not limited to F, Cl, Br, I, COH, CN, $COCH_3$, $COOCH_3$, $SO_3H$, or $NO_2$, electron donating group, for example but not limited to $OCH_3$ or $CH_3$, hydrogen (H), alkyl ($C_{1-8}$alkyl), cycloalkyl ($C_{5-7}$ cycloalkyl), and aryl, where the aryl and cycloalkyl can be substituted with the mentioned electron withdrawing or electron donating groups. The R groups on a primary amine can be H, $C_{1-8}$ alkyl, $C_{5-7}$ cycloalkyl, and aryl. Furthermore, the cycloalkyl and aryl can be substituted with any of the mentioned X and/or R groups previously mentioned. Also, the invention pertains to families of multifunctional benzoxazine monomers, as in FIG. 2, wherein $Z_1$ can be selected from —C(O)—, —S—, —O—, S(O)—, —S(O)$_2$—, or —C(CH$_3$)$_2$— on a bis-phenol or bis-amine, for example but not limited thereto. The X groups ($X_{1-4}$) of a phenol can be, for example but not limited to, an electron withdrawing group F, Cl, Br, I, COH, CN, $COCH_3$, $COOCH_3$, $SO_3H$, or $NO_2$, electron donating group $OCH_3$ or $CH_3$, unsubstituted or hydrogen (H), alkyl ($C_{1-8}$alkyl), cycloalkyl ($C_{5-7}$ cycloalkyl), and aryl, where the aryl and cycloalkyl can be substituted with (or contain) for example but not limited to the mentioned electron withdrawing and/or electron donating groups. Lastly, the R groups ($R_1$ and $R_2$) of a primary amine can be H, $C_{1-8}$ alkyl, $C_{5-7}$ cycloalkyl, and aryl, for example but not limited thereto. Furthermore, the cycloalkyl and aryl can be substituted with or contain any of the mentioned X and/or R groups previously mentioned, for example but not limited thereto.

Figure 3:
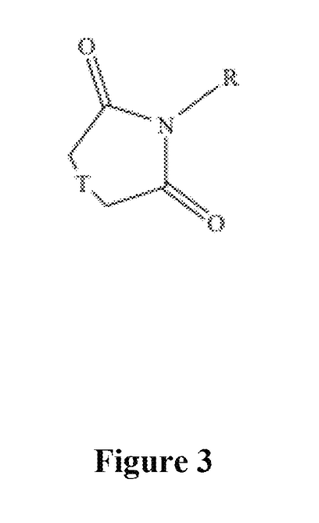
FIG. 3 depicts a monofunctional maleimide monomer general structure of the present invention.
Figure 4:
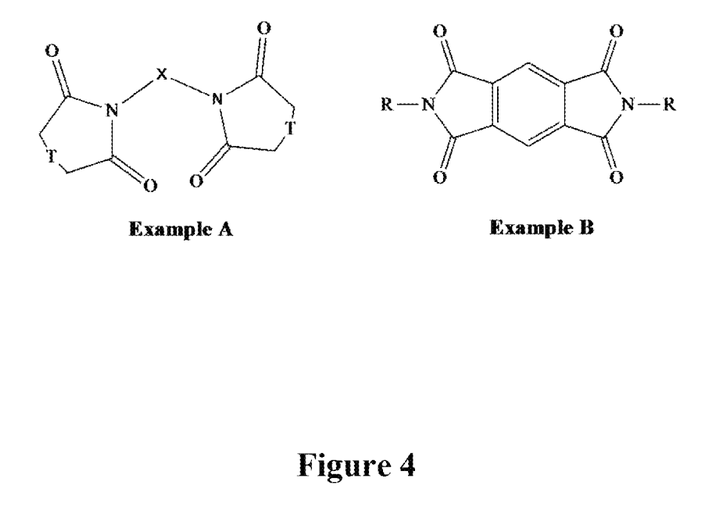
FIG. 4 depicts multifunctional bismaleimide monomer general structures of the present invention.

The present invention also relates to the melt synthesis of any variants of monofunctional maleimide monomers, as in FIG. 3, wherein T on the anhydride structure can be a double bond, a single bond, and/or contain additionally bonded substituents at either carbon of T an electron donating group, for example but not limited to, $OCH_3$ or $CH_3$, hydrogen (H), alkyl ($C_{1-8}$ alkyl), cycloalkyl ($C_{5-7}$ cycloalkyl), and aryl, where the aryl and cycloalkyl can be substituted with and/or contain the mentioned electron donating groups. The R groups on a primary amine can be, for example but not limited to H, $C_{1-8}$ alkyl, $C_{5-7}$ cycloalkyl, or aryl. Furthermore, the invention pertains to families of multifunctional bismaleimide monomers, as in FIG. 4, wherein X can be selected from —C(O)—, —S—, —O—, S(O)—, —S(O)$_2$—, or —C(CH$_3$)$_2$— on a bis-amine or bis-anhydride, for example but not limited thereto. The R groups on a primary amine can be, for example but not limited to H, $C_{1-8}$ alkyl, $C_{5-7}$ cycloalkyl, or aryl.

Figure 5:
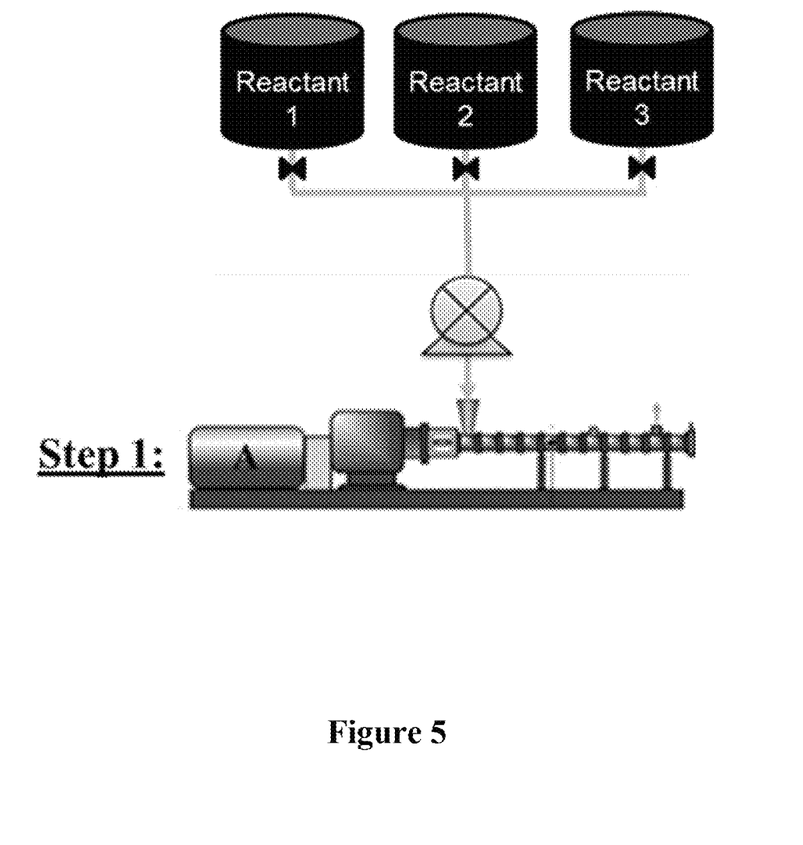
FIG. 5 depicts a schematic of the continuous high shear reactor method of the present invention.

The invention provides for the continuous high shear reactor method shown in FIG. 5, such that derivatives of the base reactants such as a meta-substituted phenol, monofunctional primary amine, and/or paraformaldehyde in molar ratios of about 1:1:4, respectively, for example, can successfully synthesize monofunctional benzoxazine monomer (Scheme A.1) or a molar ratio of 1:1 of monofunctional primary amine to maleic anhydride to synthesize monofunctional maleimide (Scheme A.2), room temperature solid and/or liquid, in about 30-60 seconds for benzoxazines and about 90 seconds for maleimides without the need for post-processing purification. The present invention therefore discloses methodology to melt synthesize monofunctional benzoxazine monomers (FIG. 1), and/or multifunctional benzoxazine monomers (FIG. 2), and/or monofunctional maleimide (FIG. 3), and/or multifunctional bismaleimide (FIG. 4) from any known variant(s) of base reactants herein, for example, fed individually and/or by pre-blended batch and utilizing a continuous high shear reactor set to processing temperatures of from about 90° C. to about 200° C. and a residence time of about 30 to 60 seconds for monofunctional and/or multifunctional benzoxazines and about 160° C. to about 300° C. and residence time of about 90 seconds for maleimides and/or bismaleimides.

Furthermore, the final benzoxazine product was comprised of over about 80% major product, Scheme A.1. The multifunctional bismaleimide final product had a high-purity and did not require post-processing purification. The process design in FIG. 5 is comprised of a reactor (FIGS. 5, 1) that is a co-rotating twin-screw extruder, for example, which is highly modular and accommodating for the change in reaction kinetics for each variant of the listed monofunctional and multifunctional benzoxazine and maleimide and bismaleimide monomers. Specifically, the reactants (Scheme A.1, Scheme B.1, and Scheme B.2), pre-blended or non-pre-blended, can be fed independently from each other or in any combinatorial option. Furthermore, the high shear environment afforded by the present invention enables the ability to effectively disperse any type of reinforcement and/or additive while synthesizing monofunctional and/or multifunctional benzoxazine and/or maleimide and/or bismaleimide monomers. Reactive diluents can be added to the synthesis at weight ratios of from about 0 to about 100 weight percent and can include, for example, monofunctional and multifunctional epoxies and curatives, or a combination thereof. Additionally, at least one reinforcement such as carbon nanotubes, graphene, POSS, silica, carbon black, and fibers, for example, and/or at least one additive such as pigments, organic matter, dispersants, molecular sieves, and flocculants, for example, or a combination thereof, can be added to the synthesis process at weighted ratios of from about 0 to about 100 weight percent. The addition of any such reinforcement and/or additive, or combination thereof, is at a weighted ratio of from about 0 to about 100 weight percent.

Utilizing the present invention, it has been demonstrated that the reaction efficiency is increased, as compared to batch reactors and other reactors from current technologies, because the major product is favored despite the ultra-high collision frequencies and the multitude of possible side reactions available in the melt (heterogeneous) synthesis of heterocyclic chemistries.

Scheme A.1: Materials used and product formed using the continuous high shear reactor Major Product Minor Product Scheme A.2: Materials used and product formed using the continuous high shear reactor

Although benzoxazine monomers have been reportedly melt synthesized in batch reactors and single-screw extruders, there is no prior work or technology that exhibits the truly "continuous" and single-step reactor design of the present invention wherein the base reactants can be fed independently and yield high purity product about 6-40× faster than currently reported. Current technology has been unable to achieve successful monomer synthesis in about 30-60 seconds at temperatures above about 100° C. as the invention. Other technologies have been unable to and have failed to increase the reaction efficiency and efficacy, favoring the major product of a potential isomeric blend, and cannot eliminate the need for post-processing purification by synthesizing high purity product utilizing the continuous high shear reactor methods disclosed in the present invention.

There are no known reports demonstrating a continuous high-shear reactor to synthesize bismaleimides under solvent-free conditions, with reactions times less than about 90 seconds and yielding a high purity product as the invention provides. The major isomer of room temperature solid and/or liquid monofunctional and/or multifunctional benzoxazine monomers can be synthesized utilizing the methods of the present invention. Moreover, the invention provides for synthesis of room temperature solid and/or liquid monofunctional and/or multifunctional benzoxazine and/or maleimide and/or bismaleimide monomers having greater than about 80% to greater than about 99% purity and eliminating the need for post-processing purification and providing the synthesis thereof in a single-step. The methodologies of the invention also provide for minimization of the formation, or even elimination, of any minor isomer.

The invention further allows for the synthesis of from about 0 to about 100 percent benzoxazine and/or maleimide and/or bismaleimide monomer alloys comprised of room temperature liquid and/or solid monofunctional and/or multifunctional benzoxazine analogues at ratios of about 0 to about 100 percent monofunctional benzoxazine monomer to multifunctional benzoxazine monomer, respectively.

Scheme B.1: Generalized reactions (I & II) to synthesize monofunctional and multifunctional benzoxazine monomer Prepolymer Scheme B.2: Generalized reactions (I & II) to synthesize multifunctional bismaleimide monomers Example A Example B Moreover, the high shear environment and modularity in screw design affords the ability to disperse any reinforcements or additives in weight percentages of about 0-99% while synthesizing these benzoxazine and/or maleimide and/or bismaleimide monomers.

The single-step solvent-free synthesis methods involving benzoxazine and bismaleimide monomer (mono functional and/or multifunctional) of the present invention with increased reaction efficiency and elimination of post-processing purification is unreported in the current scientific and patent literature. The present invention discloses cost-effective, environmentally-favorable, and scaleable design methods for the aforementioned syntheses of monofunctional and/or multifunctional benzoxazine, maleimide, and bismaleimide monomers, while also providing the ability to disperse reinforcements and additives. Such a single-step continuous reactor methodology reduces waste, batch-to-batch variations, and energy consumption, and eliminates the use of harmful solvents, although the invention may also be utilized in-solvent. Synergistically, these attributes provide a novel reactor method and market-changing opportunities for the synthesis of heterocyclic chemistries in high performance, thermoset composite industries.

In the following examples, all reactions were conducted under solvent-free conditions, while solvents could also have been used as well.

Example 1 (Monofunctional Benzoxazine Monomer)

Using reactants similar to those used in Scheme A.1 to yield an isomeric blend of monofunctional benzoxazine monomers, the phenol, amine, and paraformaldehyde were fed (unreacted) at a throughput of 0.5 kg/hr into zone 1 of the 16 mm PRISM reactor in molar ratios of 1:1:4, respectively. Zones 1-2 were set to 90° C. and zones 3-5 were set to 200° C. An unpurified aliquot was analyzed via $^1$H NMR, which confirmed that the monomer was successfully synthesized. Furthermore, the $^1$H NMR spectrum of the unpurified aliquot was compared to a $^1$H NMR spectrum of a purified aliquot analyzed in a batch reactor of the same scale and chemical species. From this comparison, it was clear that no post-processing purification was needed for the continuous reactor aliquot due to the relatively flat baseline and absence of impurity peaks. Furthermore, the continuous reactor aliquot contained less of the minor isomer, which demonstrated an increase in the reaction efficiency or favoring of the kinetic product (major isomer).

Example 2 (Monofunctional Benzoxazine Monomer)

Here, 4-methoxyphenol, m-toluidine, and paraformaldehyde were fed (unreacted) at a throughput of 0.5 kg/hr into zone 1 of the 16 mm PRISM reactor in molar ratios of 1:1:4, respectively. Zones 1-2 were set to 90° C. and zones 3-5 were set to 200° C. The screw speed was set to 60 RPM. An unpurified aliquot was analyzed via $^1$H NMR, which confirmed that the monomer was successfully synthesized.

Example 3 (Difunctional Benzoxazine Monomer)

Bisphenol-A, 3,5-dimethylaniline, and paraformaldehyde were fed (unreacted) at a throughput of 0.5 kg/hr into zone 1 of the 16 mm PRISM reactor in molar ratios of 1:2:8, respectively. Zones 1-2 were set to 90° C. and zones 3-5 were set to 200° C. The screw speed was set to 60 RPM. An unpurified aliquot was analyzed via $^1$H NMR, which confirmed that the monomer was successfully synthesized.

Example 4 (Difunctional Benzoxazine Monomer)

Here, 4,4'-(1,3-phenylenedioxy)dianiline, m-cresol, and paraformaldehyde were fed (unreacted) at a throughput of 0.5 kg/hr into zone 1 of the 16 mm PRISM reactor in molar ratios of 1:2:8, respectively. Zones 1-2 were set to 90° C. and zones 3-5 were set to 205° C. The screw speed was set to 60 RPM. An unpurified aliquot was analyzed via H NMR, which confirmed that the monomer was successfully synthesized.

Example 5 (Difunctional Bismaleimide Monomer)

Here, 4,4'-diaminodiphenylsulfone and lindride 52D were fed (unreacted) at a throughput of 0.5 kg/hr into zone 1 of the 16 mm PRISM reactor in molar ratios of 1:2, respectively. Zones 1-2 were set to 200° C. and zones 3-5 were set to 300° C. The screw speed was set to 60 RPM. An unpurified aliquot was analyzed via $^1$H NMR, which confirmed that the monomer was successfully synthesized.

The above detailed description is presented to enable any person skilled in the art to make and use the invention. Specific details have been revealed to provide a comprehensive understanding of the present invention, and are used for explanation of the information provided. These specific details, however, are not required to practice the invention, as is apparent to one skilled in the art. Descriptions of specific applications, analyses, and calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

The compositions, processes, systems, and methods of the present invention are often best practiced by empirically determining the appropriate values of the operating parameters, or by conducting simulations to arrive at best design for a given application. Accordingly, all suitable modifications, combinations, and equivalents should be considered as falling within the spirit and scope of the invention.

REFERENCES

Agag, T.; Geiger, S.; Alhassan, S. M.; Qutubuddin, S.; Ishida, H., *Macromolecules* 2010, 43 (17), 7122-7127.
Allen, D. J.; Ishida, H., *Polymer* 2009, 50 (2), 613-626.
Andersen, P. G.; Lechner, F., *Proc. SPE* 2013.
Baranek, A. D. Design and synthesis of flexible and functional polybenzoxazine thin films. Ph.D., The University of Southern Mississippi, Ann Arbor, 2013.
Brunovska, Z.; Liu, J. P.; Ishida, H., *Macromol. Chem. Phys.* 1999, 200 (7), 1745-1752.
Burke, W. J.; Weatherbee, C., *J. Am. Chem. Soc.* 1950, 72 (10), 4691-4694.
Burke, W. J., *J. Am. Chem. Soc.* 1949, 71 (2), 609-612.
Burke, W. J.; Stephens, C. W., *J. Am. Chem. Soc.* 1952, 74 (6), 1518-1520.
Burke, W. J.; Bishop, J. L.; Glennie, E. L. M.; Bauer, W. N., *J. Org. Chem.* 1965, 30 (10), 3423-3427.
Cai, C.; Shi, Q.; Li, L.; Zhu, L.; Yin, J., *Radiat. Phys. and Chem.* 2008, 77 (3), 370-372.
Easton, R. W. British Patent No. 109,663. 1916.
Easton, R. W. U.S. Pat. No. 1,468,379. 1923.
Fang, H.; Ma, X.; Feng, L.; Wang, K.; Cao, B., *J. Appl. Polym. Sci.* 2008, 108 (6), 3652-3661.
Finnigan, B.; Martin, D.; Halley, P.; Truss, R.; Campbell, K., *Polymer* 2004, 45 (7), 2249-2260.
Higginbottom, H. P. Polymerizable compositions comprising polyamines and poly(dihydrobenzoxazines). 1988.
Higginbottom, H. P.; Drumm, M. F. Process for deposition of resin dispersions on metal substrates. 1988.
Holly, F. W.; Cope, A. C., *J. Am. Chem. Soc.* 1944, 66 (11), 1875-1879.
Ishida, H. A., T, *Handbook of Benzoxazine Resins*. Elsevier: Amsterdam, 2011; Vol. 1.
Ishida, H., Process for preparation of benzoxazine compounds in solventless systems, U.S. Pat. No. 5,543,516, Aug. 6, 1996.
Kimura, H.; Ohtsuka, K.; Matsumoto, A., Chapter 24—Poly (Benzoxazine/Bisoxazoline). *Handbook of Benzoxazine Resins*, Agag, H. I., Ed. Elsevier: Amsterdam, 2011; pp 429-441.
Moad, G., *Prog. Polym. Sci.* 1999, 24 (1), 81-142.
Ning, X.; Ishida, H., *J. Polym. Sci. Part A: Polym. Chem.* 1994, 32 (6), 1121-1129.
Prat, L.; N'Diaye, S.; Rigal, L.; Gourdon, C., *Chemical Engineering and Processing: Process Intensification* 2004, 43 (7), 881-886.
Rimdusit, S.; Jongvisuttisun, P.; Jubsilp, C.; Tanthapanichakoon, W., *J Appl. Polym. Sci.* 2009, 111 (3), 1225-1234.
S. B. Brown, C. M. O., Reactive Extrusion. *Encyclopedia of Polymer Science and Engineering*, John Wiley: New York, 1988; Vol. 14, p 169.
Schreiber, H. German Patent 2,255,504. 1973.
Schreiber, H. Polymeric resins derived from 1-oxa-3-aza tetraline group-containing compounds and cycloaliphatic epoxides. 1986.
Shokoohi, S.; Arefazar, A.; Naderi, G., *Mat. Des.* 2011, 32 (3), 1697-1703.
Titier, C.; Pascault, J.-P.; Taha, M., *J. Appl. Polym. Sci.* 1996, 59 (3), 415-423.
Tzoganakis, C., *Adv. Polym. Tech.* 1989, 9 (4), 321-330.
Wang, Y.-X.; Ishida, H., *J. Appl. Polym. Sci.* 2002, 86 (12), 2953-2966.
Ward, S.; Harriman, M. Benzoxazines and Compositions Containing the Same. US Patent Application 2013/026759. 2013.
Wunsche, A. German Patent 131,392. 1901.
Xanthos, M., *Reactive extrusion: principles and practice*. Hanser Publishers; Distributed in the USA and Canada by Oxford University Press: Munich; New York N.Y., 1992; p xv, 304 p.

Yeganeh, H., Chapter 21—Polybenzoxazine/Polyurethane Alloys. *Handbook of Benzoxazine Resins*, Agag, H. I., Ed. Elsevier: Amsterdam, 2011; pp 389-403.

Zhang, C.; Wang, L.; Yu, R.; Zheng, S., Chapter 25—Morphology and Properties of Polybenzoxazine Blends. *Handbook of Benzoxazine Resins*, Agag, H. I., Ed. Elsevier: Amsterdam, 2011; pp 445-455.

What is claimed is:

1. A method to melt synthesize a monofunctional benzoxazine monomer, maleimide monomer, or both, from a known variant of at least one base reactant, the method comprising:
   utilizing in a reactor at least one base reactant from a batch of pre-blended reactants for the synthesis, wherein the at least one base reactant is a phenol, amine, paraformaldehyde, or a combination thereof, and
   forming the monofunctional benzoxazine monomer, maleimide monomer, or both, using a continuous, high shear reactor at a processing temperature of from about 90° C. to about 200° C. and a residence time of about 30 to about 60 seconds for benzoxazines and about 160° ° C. to about 300° C. and a residence time of about 90 seconds for maleimides,
   wherein the monofunctional benzoxazine monomer, maleimide monomer, or both, is a room temperature solid and the chemical structure of the benzoxazine monomer is:

where substituents $X_{1-4}$ on phenol are X groups and can be an electron withdrawing group selected from the group consisting of F, Cl, Br, I, COH, CN, COCH$_3$, COOCH$_3$, SO$_3$H, and NO$_2$, or an electron donating group selected from the group consisting of OCH$_3$ or CH$_3$, hydrogen (H), alkyl ($C_{1-8}$ alkyl), cycloalkyl ($C_{5-7}$ cycloalkyl), and aryl, and where the aryl and the cycloalkyl can also include or contain substituents such as and from the electron withdrawing group or the electron donating group, or both, and the R is at least one group on a primary amine and can be selected from the group consisting of H, $C_{1-8}$ alkyl, $C_{5-7}$ cycloalkyl, and aryl, and the aryl and the cycloalkyl can be substituted with or contain any of the X groups, R groups, or both, and the chemical structure of the maleimide monomer is:

where T on the anhydride structure can be a double bond, a single bond or can contain additionally bonded substituents at either carbon of T, an electron donating group selected from the group consisting of OCH$_3$ or CH$_3$, hydrogen (H), alkyl ($C_{1-8}$ alkyl), cycoakyl ($C_{5-7}$ cycloalkyl), and aryl and where the aryl and the cycloalkyl can be substituted with or contain any substituents such as and from the electron donating group, and the R is at least one group on a primary amine and can be selected from the group consisting of H, $C_{1-8}$ alkyl, $C_{5-7}$ cycloalkyl, and aryl.

2. The method of claim 1, wherein the at least one base reactant is fed to the reactor independently from at least one other base reactant.

3. The method of claim 2, wherein the monofunctional benzoxazine monomer, maleimide monomer, or both, is a room temperature liquid.

4. The method of claim 1, further comprising melt synthesizing the major isomer of the monofunctional benzoxazine monomer, maleimide monomer, or both, wherein the monomer is a room temperature solid, and minimizing the formation of any minor isomer.

5. The method of claim 1, further comprising melt synthesizing the major isomer of the monofunctional benzoxazine monomer, maleimide monomer, or both, wherein the monomer is a room temperature liquid, and minimizing the formation of any minor isomer.

6. A method to melt synthesize a multifunctional benzoxazine monomer, bismaleimide monomer, or both, from a known variant of at least one base reactant, the method comprising:
   utilizing in a reactor at least one base reactant from a batch of pre-blended reactants for the synthesis, wherein the at least one base reactant is a phenol, amine, paraformaldehyde, or a combination thereof, and
   forming the multifunctional benzoxazine monomer, bismaleimide monomer, or both, using a continuous, high shear reactor at a processing temperature of from about 90° C. to about 200° C. and a residence time of about 30 to about 60 seconds for benzoxazines and about 160° C. to about 300° C. and a residence time of about 90 seconds for bismaleimides,
   wherein the multifunctional benzoxazine monomer, bismaleimide monomer, or both, is a room temperature solid and the chemical structure of the multifunctional benzoxazine monomer is either of the chemical structures of Example A or Example B:

Example A

Example B where $Z_1$ is selected from the group consisting of —C(O)—, —S—, —O—, S(O)—, —S(O)$_2$—, and —C(CH$_3$)$_2$— on a bis-phenol or bis-amine, the X groups $X_{1-4}$ of a phenol are selected from the group consisting of an electron withdrawing group selected from the group consisting of F, Cl, Br, I, COH, CN, COCH$_3$, COOCH$_3$, SO$_3$H, and NO$_2$, or an electron donating group selected from the group consisting of $OCH_3$ or $CH_3$, unsubstituted or hydrogen (H), alkyl ($C_{1-8}$ alkyl), cycloalkyl ($C_{5-7}$ cycloalkyl), and aryl, and where the aryl and the cycloalkyl can also include or contain substituents such as and from the electron withdrawing group or the electron donating group, or both, and the R groups $R_1$ and $R_2$ of primary amine and can be selected from the group consisting of H, $C_{1-8}$ alkyl, $C_{5-7}$ cycloalkyl, and aryl, and the aryl and the cycloalkyl can be substituted with or contain any of the X groups, R groups, or both, and the chemical structure of the multifunctional bismaleimide monomer is either of the chemical structures of Example A or Example B:

Example A

Example B where X can be selected from the group consisting of —C(O)—, —S—, —O—, S(O)—, —S(O)$_2$—, and —C(CH$_3$)$_2$— on a bis-amine or bis-anhydride and the R is at least one group on a primary amine and can be selected from the group consisting of H, $C_{1-8}$ alkyl, $C_{5-7}$ cycloalkyl, and aryl.

7. The method of claim 6, wherein the at least one base reactant is fed to the reactor independently from at least one other base reactant.

8. The method of claim 7, wherein the multifunctional benzoxazine monomer, bismaleimide monomer, or both, is a room temperature liquid.

9. The method of claim 6, further comprising melt synthesizing the major isomer of the multifunctional benzoxazine monomer, bismaleimide monomer, or both, wherein the monomer is a room temperature solid, and minimizing the formation of any minor isomer.

10. The method of claim 6, further comprising melt synthesizing the major isomer of the multifunctional benzoxazine monomer, bismaleimide monomer, or both, wherein the monomer is a room temperature liquid, and minimizing the formation of any minor isomer.

11. The method of claim 1, wherein the synthesis is in a single-step and the monofunctional benzoxazine monomer, maleimide monomer, or both, that is formed is from about 80% to about 99% purity, thereby eliminating the need for post-processing purification.

12. The method of claim 1, wherein the synthesis is in a single-step and the monofunctional benzoxazine monomer, maleimide monomer, or both, that is formed is a room temperature liquid and is from about 80% to about 99% purity, thereby eliminating the need for post-processing purification.

13. The method of claim 6, wherein the synthesis is in a single-step and the multifunctional benzoxazine monomer, bismaleimide monomer, or both, that is formed is from about 80% to about 99% purity, thereby eliminating the need for post-processing purification.

14. The method of claim 6, wherein the synthesis is in a single-step and the multifunctional benzoxazine monomer, bismaleimide monomer, or both, that is formed is a room temperature liquid and is from about 80% to 99% purity, thereby eliminating the need for post-processing purification.

15. A method of synthesis of about 100% benzoxazine monomer alloy, bismaleimide monomer alloy, or both, as a final product, the method comprising:
forming the alloy from a monofunctional benzoxazine monomer analogue or a maleimide monomer analogue and a multifunctional benzoxazine monomer analogue or a bismaleimide monomer analogue using a continuous, high shear reactor at a processing temperature of from about 90° C. to about 200° C. and a residence time of about 30 to about 60 seconds for benzoxazines and about 160° C. to about 300° C. and a residence time of about 90 seconds for maleimides and bismaleimides,
wherein the monofunctional benzoxazine monomer analogue or maleimide monomer analogue is a room temperature solid or a room temperature liquid and the multifunctional benzoxazine monomer analogue or bismaleimide monomer analogue is a room temperature solid or a room temperature liquid and wherein the ratio of monofunctional benzoxazine monomer or maleimide monomer to multifunctional benzoxazine monomer or bismaleimide monomer is about 0 to about 100 percent and wherein the about 100% benzoxazine alloy is comprised of only chemical structures containing oxazine moieties and the about 100% bismaleimide alloy is comprised of only chemical structures containing the —C(O)NRC(O)— functional group.

16. The method according to any of claims 1 through 15, further comprising adding to the synthesis a reactive diluent at a weight ratio of up to about 100 weight percent, wherein the reactive diluent is a monofunctional or multifunctional epoxy, a monofunctional or multifunctional curative, or a combination thereof, and optionally adding to the synthesis at least one reinforcement from the group consisting of carbon nanotubes, graphene, POSS, silica, carbon black, and fibers, at least one additive from the group consisting of pigments, organic matter, dispersants, molecular sieves, and flocculants, or a combination of at least one reinforcement and at least one additive thereof, wherein the addition of any reinforcement or additive is at a weighted ratio of from about 0 to about 100 weight percent and the synthesis is in-solvent or is solvent-free for reducing isomer formation.

* * * * *